United States Patent [19]
Bachman et al.

[11] Patent Number: 5,733,265
[45] Date of Patent: Mar. 31, 1998

[54] SHIELDED NEEDLE ASSEMBLY

[75] Inventors: Alan B. Bachman; Jeffrey A. Stein, both of Woodbridge, Conn.

[73] Assignee: Becton Dickinson and Company, Franklin Lakes, N.J.

[21] Appl. No.: 719,222

[22] Filed: Sep. 25, 1996

[51] Int. Cl.$^6$ .................................................. A61M 5/32
[52] U.S. Cl. .............................. 604/263; 604/192
[58] Field of Search .............................. 604/263, 192, 604/187, 110

[56] References Cited

U.S. PATENT DOCUMENTS

| | | | |
|---|---|---|---|
| 4,982,842 | 1/1991 | Hollister | 206/365 |
| 5,116,325 | 5/1992 | Paterson | 604/263 X |
| 5,188,611 | 2/1993 | Orgain | 604/192 |
| 5,207,653 | 5/1993 | Janjua et al. | 604/192 |
| 5,312,369 | 5/1994 | Arcusin et al. | 604/192 |
| 5,486,163 | 1/1996 | Haynes | 604/263 X |

*Primary Examiner*—John D. Yasko
*Attorney, Agent, or Firm*—Arthur D. Dawson

[57] ABSTRACT

A needle assembly includes an elongate needle, a needle hub with an axial bore therethrough to receive and hold the needle projecting axially, the needle hub further is releasably mountable on a fluid handling device. The assembly has an elongate shield having an open proximal end, a distal end and a sidewall with an inside surface defining a cavity. There is an elongate aperture into the cavity from about the distal end to the proximal end. The assembly has a hinge that includes a mount for retaining the shield onto the hub, the mount has an opening therein that is sized and shaped to receive at least a portion of the needle hub. The shield is movable about the hinge by an off-axis pivotal movement between an initial closed position, an open position and a latched position. The assembly has a removable cover that is disposed over the elongate aperture in the shield and engaging the shield to hold it in the initial closed position. The cover is removable by a distal axial movement that also opens the shield, disengages the cover from the shield exposes at least the distal point of the needle. There is a latch for latching the shield to the mount when the shield is in the latched position.

20 Claims, 16 Drawing Sheets

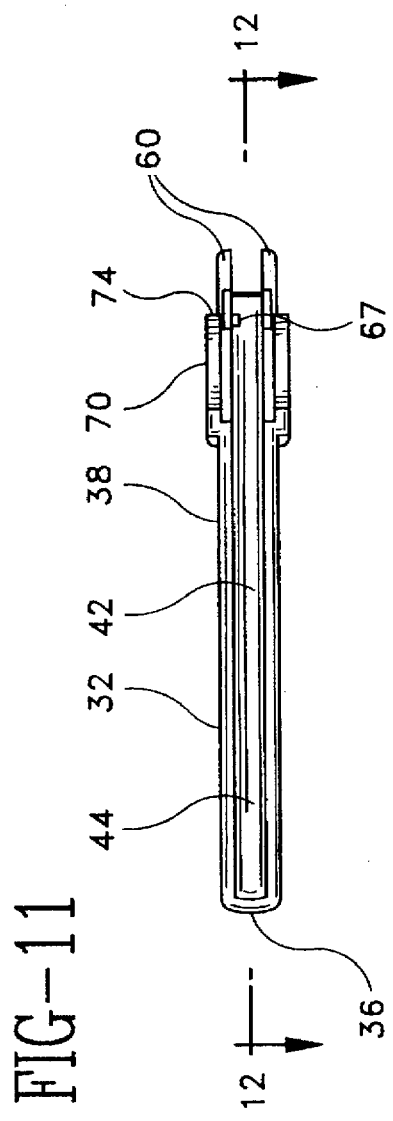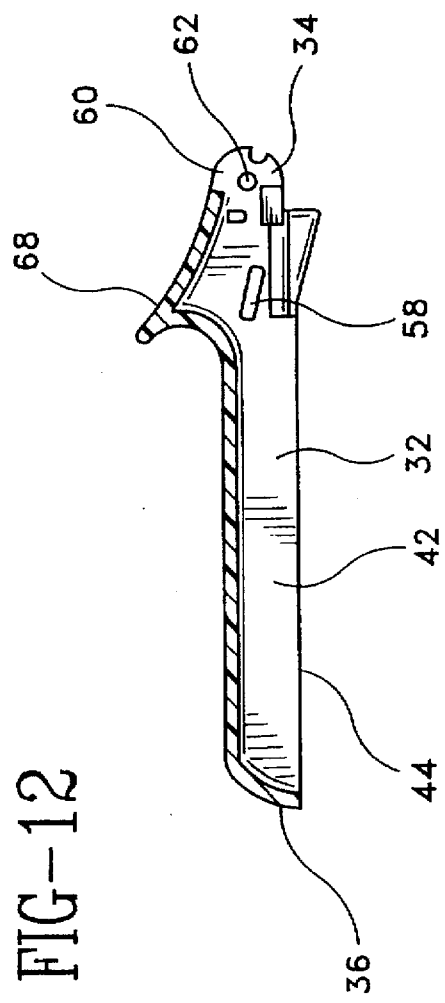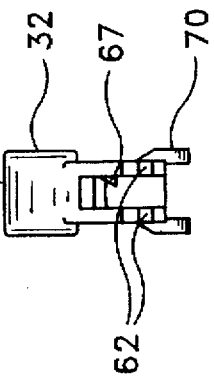

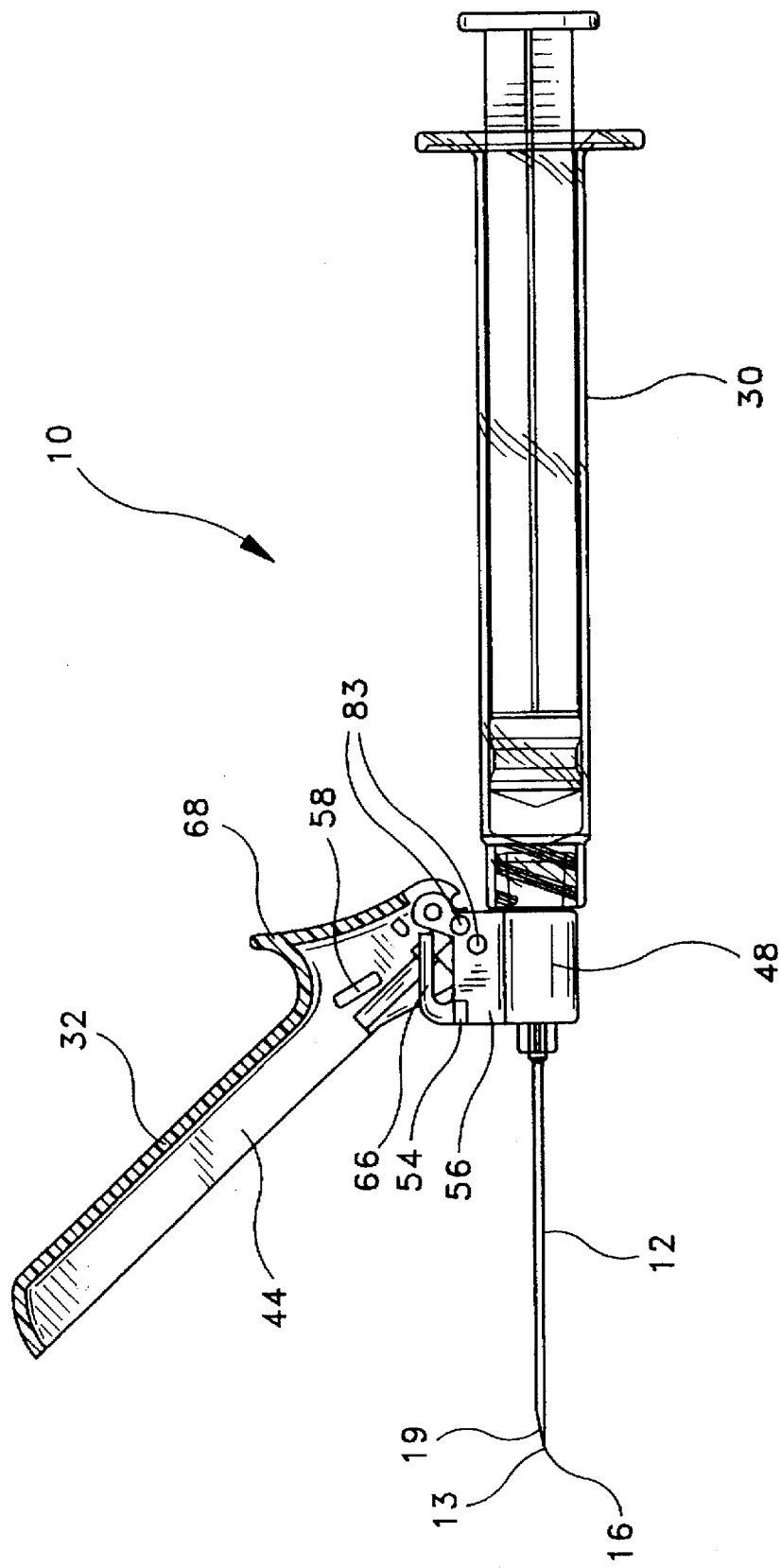

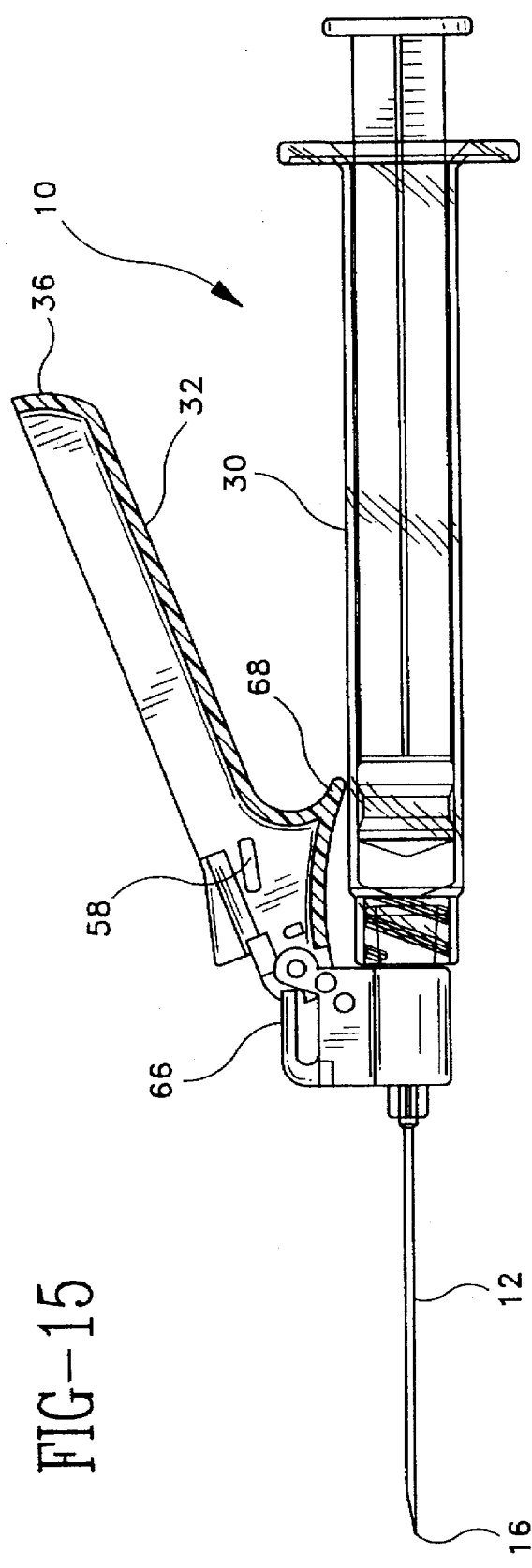
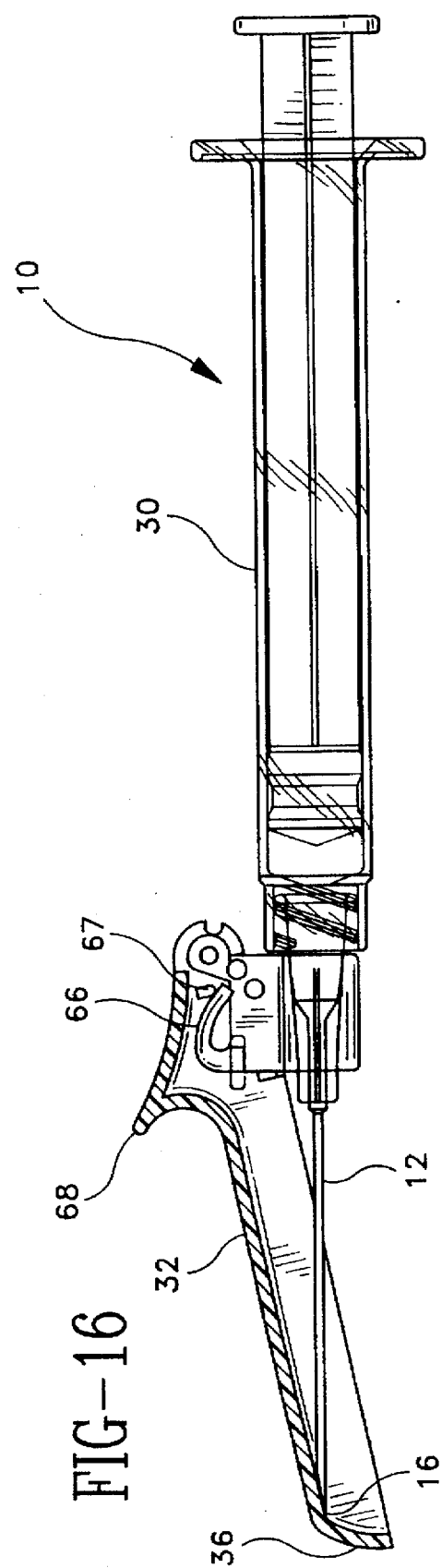

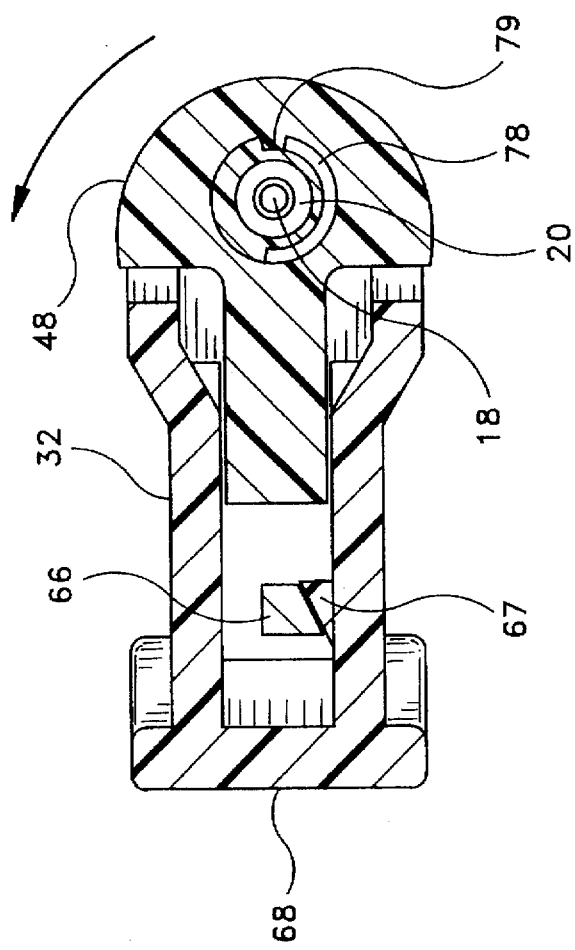
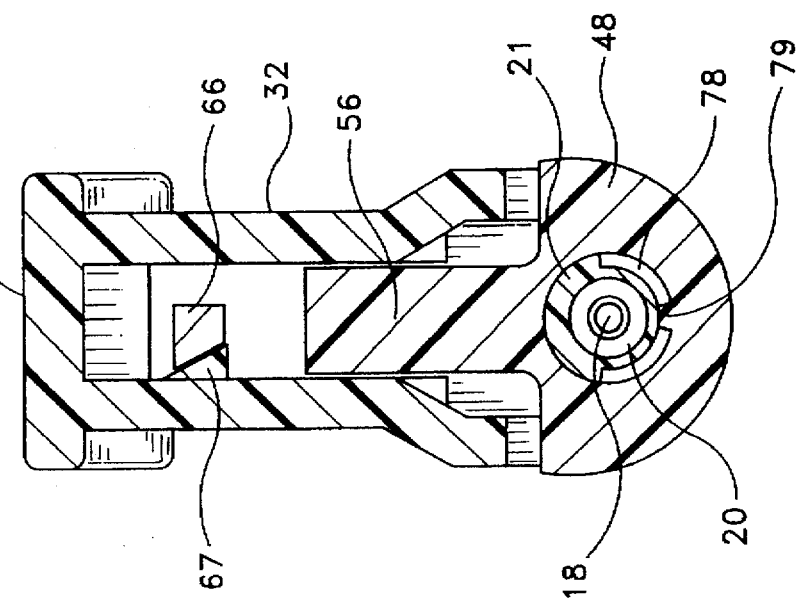

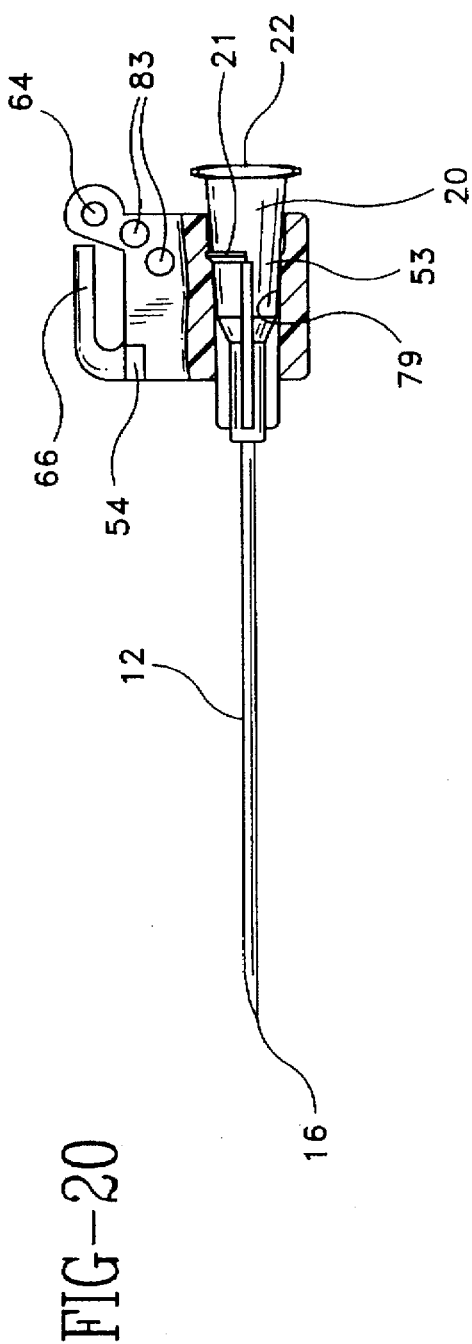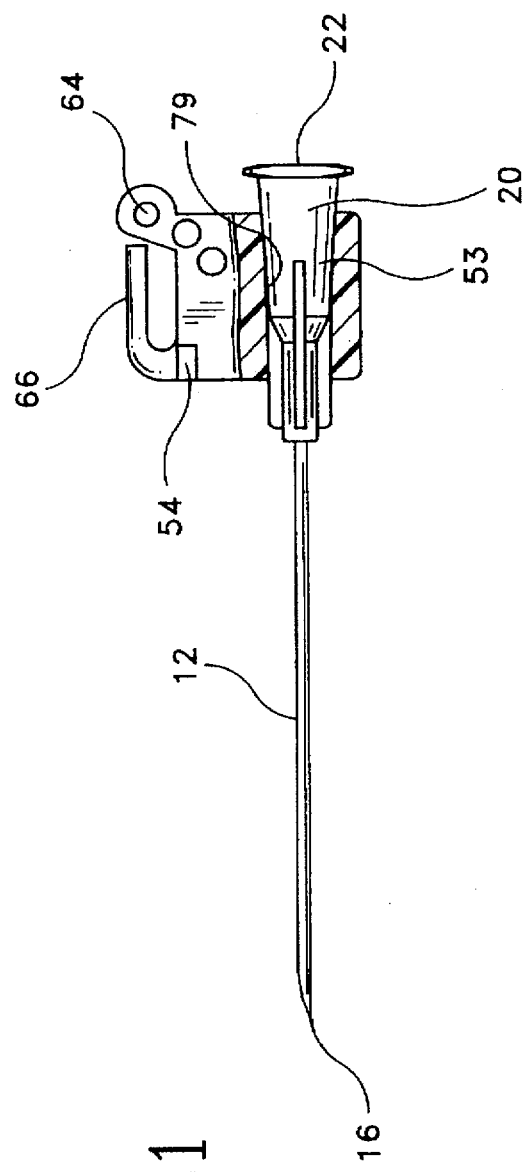

5,733,265

SHIELDED NEEDLE ASSEMBLY

FIELD OF INVENTION

The present invention relates to a protective shield for a needle and more particularly to a shielded needle assembly that includes the hub of the needle, and allows use of the needle on a syringe, needle holder or other fluid handling device.

DESCRIPTION OF RELATED INFORMATION

In the medical arts, sharp pointed needles are used in many procedures. Devices having sharp pointed needles are used for administering fluids to patients either directly or into intravenous apparatus, and in various blood drawing applications either with syringes or with specialized holders for filling evacuated tubes. Since needles are so widely used in medical procedures, many people are potentially exposed to needles in the routine course of their work. These needle exposures are not limited only to the practitioners directly involved in patient treatment, but also include support workers all through the hospital. These support workers include hospital pharmacy technicians, who prepare dosages, and hospital service personnel, such as laundry, housekeeping, etc.

Needle exposure problems are not just limited to needle sticks from already used needles. Hospital pharmacy workers often prepare syringes with doses of costly medications, recap the syringe, and transport the syringe with the dose to the patient. If the pharmacy worker inadvertently sticks himself or damages the needle, the syringe and the dose is likely rendered unusable. Exposure to blood borne pathogens should be a recognized hazard by anyone associated with the medical arts. As a result of this recognition, numerous protocols for use of needles have been developed and are widely practiced. The problem of transmission of blood borne pathogens not only exists for the physician, nurse or phlebotomist using the needles, but also for support workers all through the hospital.

The use protocols generally dictate in detail when and how a needle is used and how it should be disposed of. The problem with many protocols for handling needles is that the protocols often require users to perform additional steps in a procedure. With the press of time and simple carelessness, certain practices regarding handling of used needles are sometimes disregarded and injuries still occur. The medical device industry has responded to the problem by producing a wide variety of sharps collectors, needle shielding devices and the like to assist practitioners in their need to reduce the occurrence of needle injuries.

Many devices have been developed for shielding needles after use to avoid exposing people to used needles. A representative listing of many of these devices is found in U.S. Pat. No. 4,982,842 to Hollister et al. Hollister et al. discloses a stand alone adapter that has a male and female end for mating with a needle assembly and the ejection end of a syringe. The device of Hollister et al. includes a housing mounted to the adapter which may be pivoted to a position in alignment with the needle for enveloping the needle and locking the needle to retain it in the housing. The Hollister et al. device increases the unusable or "dead-space" volume of the device on which the adapter is mounted, and requires an additional part that increases the projection of the needle hub. Also, if bevel position is important to the intended use of the needle, the Hollister et al. invention must be carefully aligned with the needle point when mounted.

U.S. Pat. No. 5,207,653 to Janjua et al. discloses a needle cap with a longitudinal slit having a width greater than the width of a needle. According to Janjua et al., the needle cap is adapted to be pivotally connected with the needle and hub piece. Janjua et al. also discloses that the needle cap is usable with a syringe or with a needle holder for fluid collection tubes. The device disclosed by Janjua et al. mounts on the needle hub with a pivot, but since it only pivots in one plane, unless the needle point is precisely oriented with the hub during assembly, the shield may interfere in some applications.

Most of the devices listed in the background of the Hollister et al. patent, the Hollister et al. invention itself and the Janjua et al. invention, attempt to address the recognized need to protect medical and service personnel from needle sticks. There are several recurrent problems in varying degrees with these devices. Many of these previous devices are somewhat complex, hence are significantly more costly than an unprotected device. Many of these previous devices also increase the complexity or increase the difficulty of performing a procedure. Some others of the previous devices are so procedure specific that they preclude use of the device in certain other procedures. For these and similar reasons most of the devices disclosed in the Hollister et al. background have never been successfully commercialized.

Blood drawing is one application that is particularly sensitive to needle point orientation. Most phlebotomists carefully align a needle point with the beveled face away from the skin so that the needle point placement may be precisely controlled. A needle assembly as disclosed in Janjua et al. would either sometimes be clumsy to use because the shield would sometimes be in the way or, alternatively, more expensive because of the need to carefully orient the point during manufacture. Additionally, in the Janjua et al. patent, while there is a recognition of the need to secure the cap in the closed position over the needle, all of the solutions proposed require additional steps such as securing the cap with an adhesive or twisting the cap.

Although there already are many shielded needle devices, there is still a need for a shielded needle device that is easily manufactured, applicable to many types of fluid handling devices, as well as simple and intuitive to use. Additionally, the needle device should not interfere with normal practices of use. Such a device is described below.

SUMMARY

A needle assembly of the present invention includes an elongate needle that has a proximal end, a distal end and a passageway therethrough that defines an axis. The assembly has a needle hub with a proximal end, a distal end and an exterior surface. The needle hub has an axial bore therethrough to receive and hold the needle with the distal end projecting axially. The proximal end of the needle hub is releasably mountable on a fluid handling device. The assembly includes an elongate shield with an open proximal end, a distal end and a sidewall with an inside surface defining a cavity. The sidewall has an elongate aperture into the cavity from about the distal end to the proximal end. There is a hinge that includes a mount for retaining the shield onto the hub. The mount includes an opening that is sized and shaped to receive at least a portion of the needle hub. The hinge allows off-axis pivotal movement between an initial closed position that substantially prevents inadvertent access to the needle, an open position wherein at least the distal point of the needle is exposed and a latched position wherein the shield is in contact with the needle, is latched to the mount and substantially prevents access to the distal point of the needle. The assembly also has a removable cover that is disposed over the elongate aperture in the shield and engages the shield to hold it in the initial closed position. The cover is removable by a distal axial movement that opens the shield, disengages the cover from the shield and exposes at least the distal point of the needle. There is a latch for latching the shield to the mount when the shield is latched.

Practitioners find that the shielded needle assembly of the invention is intuitive to use. To expose the needle for use, the practitioner simply grasps the cover and pulls it off distally. The cover may then be discarded, the same as is done with the shield of a conventional shielded needle. Removal of the cover causes the needle shield to pivot open and exposes the needle for use. After the cover is removed, it can be replaced to protect the needle for transporting the needle to the treatment location without the shield being closed. This ability to protect the needle after opening is important for hospital pharmacy applications, i.e., where the syringe is filled and must be transported to a remote location for use. Since the shield is partially opened, it is visually apparent that the syringe is being used. When the practitioner has completed the procedure with the needle, the shield is latched by simply pivoting the shield onto the needle until it touches the needle and latches. During the latching, practitioners do not need to position their hands beyond the point of the needle, the shield is easily closed and latched with the practitioners' hands located proximal to the sharp needle point.

BRIEF DESCRIPTION OF THE DRAWINGS

FIG. 11 is a bottom plan view of the shield portion of the assembly of the invention;

FIG. 12 is a cross-sectional view of the shield portion of the assembly of the invention taken from FIG. 11 along the line 12—12;

FIG. 13 is a proximal end view of the shield portion of the assembly of the invention;

FIG. 14 is a partial cross-sectional view of the assembly of the invention mounted on a fluid handling device with the shield partially open taken from FIG. 3 along the line 14—14;

FIG. 15 is a partial cross-sectional view of the assembly of the invention mounted on a fluid handling device with the shield fully open taken from FIG. 4 along the line 15—15;

FIG. 16 is a partial cross-sectional view of the assembly of the invention mounted on a fluid handling device with the shield latched taken from FIG. 5 along the line 16—16;

FIG. 17 is a cross-sectional view of the assembly of the invention taken from FIG. 1 along the line 17—17;

FIG. 18 is a cross-sectional view of the assembly of the invention analogous to FIG. 17 having the mount rotated with respect to the needle hub;

FIG. 20 is a partial cross-sectional view of the mount and hub portion of the assembly of FIG. 1;

FIG. 21 is a partial cross-sectional view of the mount and hub portion of an embodiment of the invention analogous to the view of FIG. 20;

DETAILED DESCRIPTION

Figure 1:
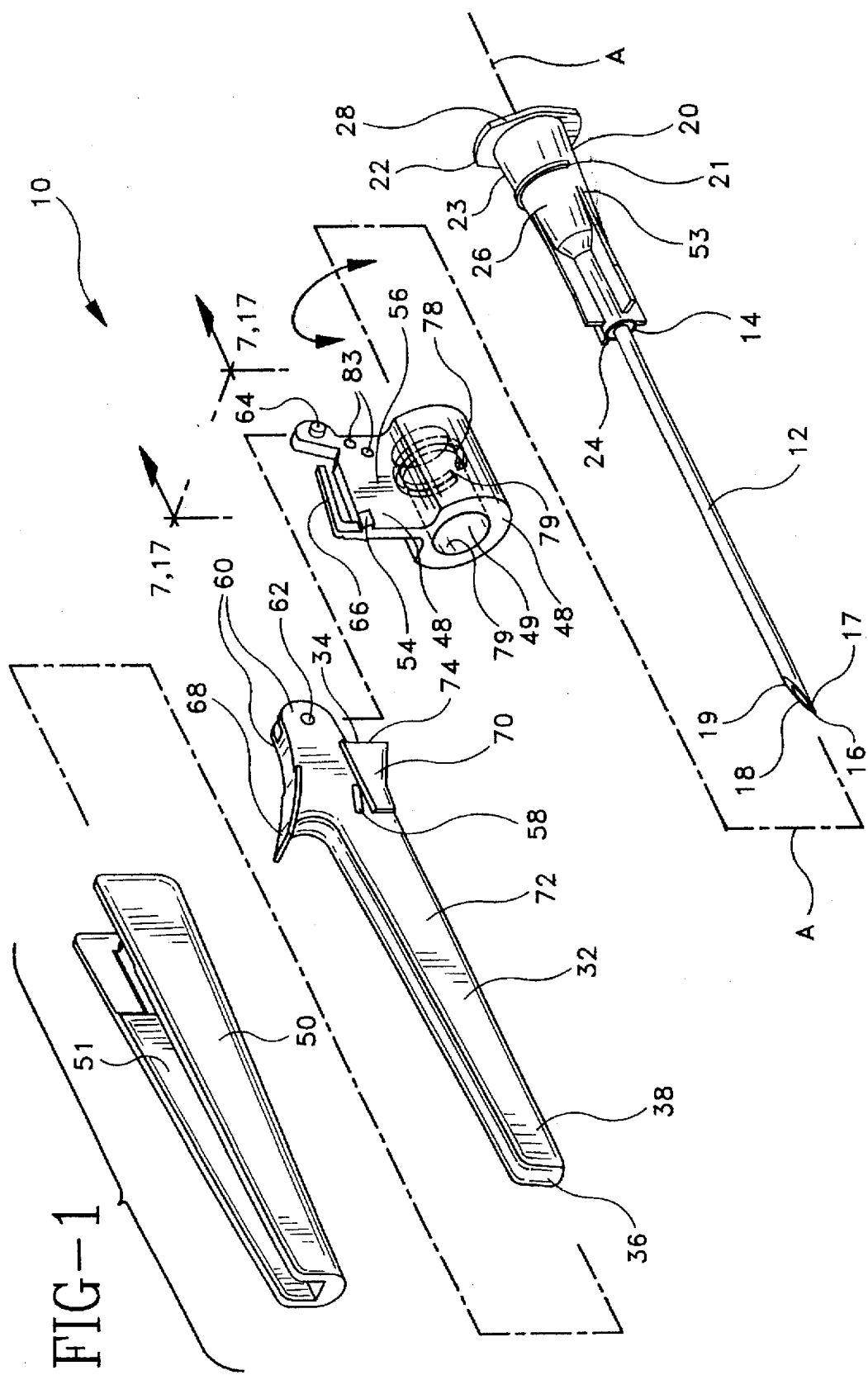
FIG. 1 is a partially exploded perspective view of the preferred shielded needle assembly of the present invention.

While this invention is satisfied by embodiments in many different forms, there is shown in the drawings and described herein in detail, preferred embodiments of the invention with the understanding that the present disclosure is to be considered exemplary of the principles of the invention and is not intended to limit the invention to the embodiments illustrated. The scope of the invention is to be measured by the appended claims and their equivalents. In this description, a convention is followed wherein the term "proximal" refers to the portion of the device closest to the practitioner and the term "distal" refers to portion of the device away from the practitioner.

Figure 5:
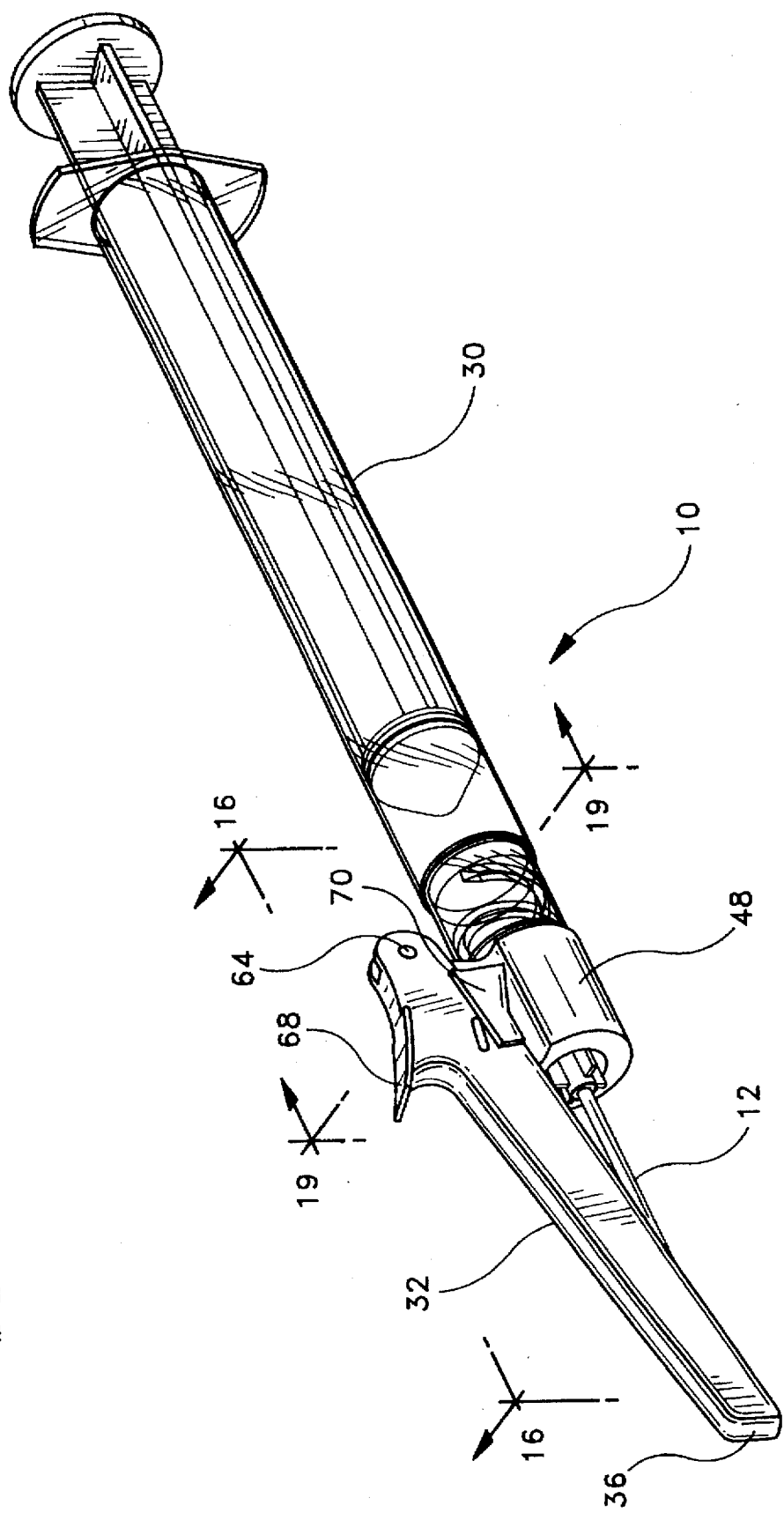
FIG. 5 is a perspective view of the assembly of the invention mounted on a fluid handling device and with the shield in the latched position.

Referring to FIGS. 1–20, a needle assembly 10 of the present invention includes an elongate needle 12 with a proximal end 14, a distal end 16 and a passageway 18 therethrough that defines an axis A. Assembly 10 includes a needle hub 20 with a proximal end 22, a distal end 24 and an exterior surface 26. Needle hub 20 has an axial bore 28 to receive and hold needle 12 with distal end 16 of the needle, preferably having a sharp point 17, projecting axially. Proximal end 22 of the needle hub is releasably mountable, preferably with a female luer fitting on a fluid handling device such as a syringe 30. Assembly 10 has an elongate shield 32 with an open proximal end 34, a preferably closed distal end 36 and a sidewall 38 with an inside surface 40 and an outside surface 41 that defines a cavity 42. Sidewall 38 has an elongate aperture 44 into cavity 42 from about distal end 36 to proximal end 34. Assembly 10 has a hinge 46 that includes a mount 48 for retaining shield 32 onto hub 20, mount 48 also includes an opening 49 therein that is sized and shaped to receive at least a portion 53 of needle hub 20. Shield 32 is movable about hinge 46 by an off-axis pivotal movement between an initial closed position, best seen in FIGS. 2 and 6, wherein inadvertent access to needle 12 is substantially prevented; an open position, best seen in FIGS. 3, 4, 14 and 15 wherein at least sharp distal point 17 of the needle is exposed; and a latched position, best seen in FIGS. 5, 16 and 19 wherein shield 32 is in contact with needle 12, is latched to mount 48, and substantially prevents access to sharp distal point 17 of the needle.

Figure 2:
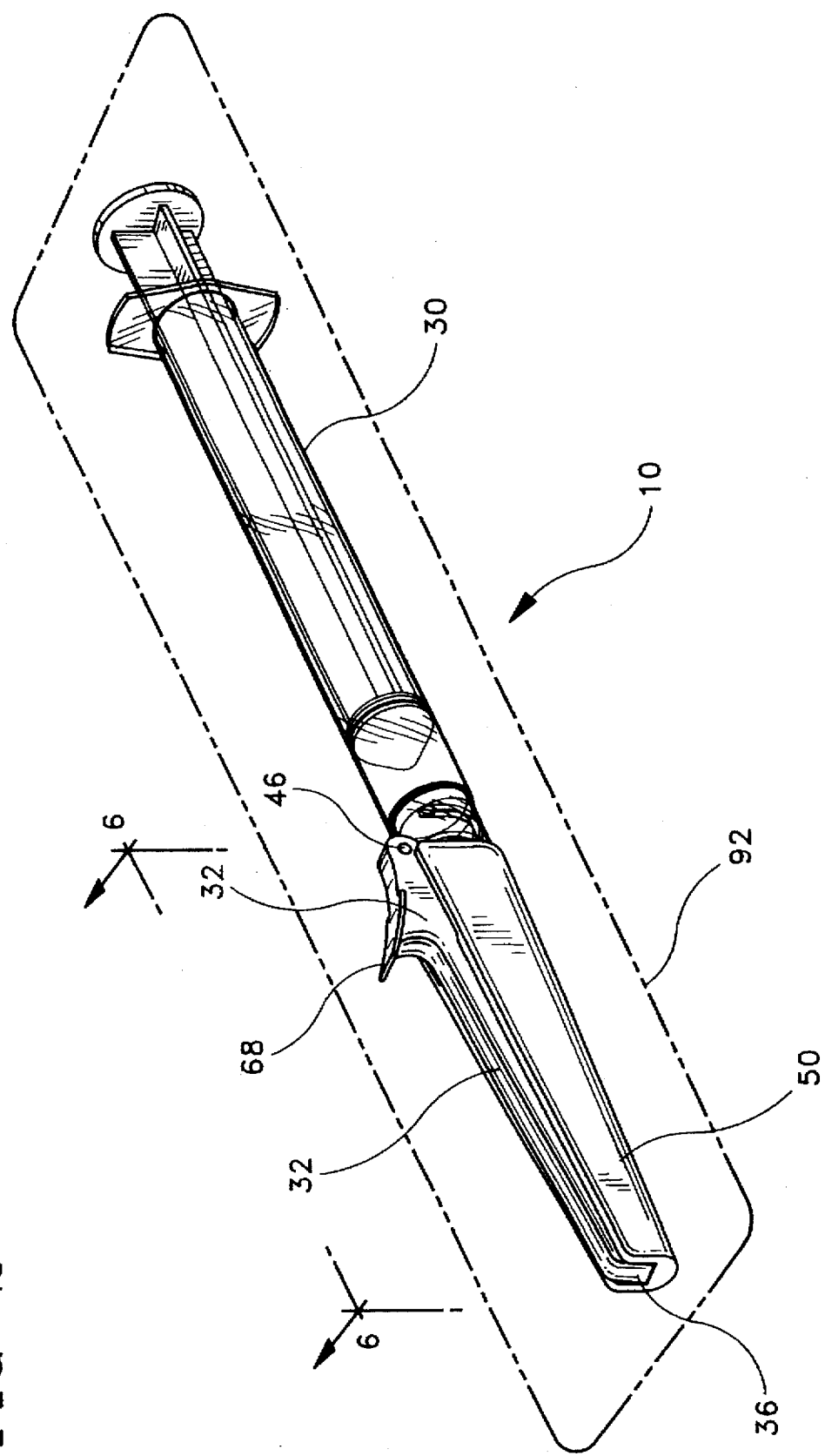
FIG. 2 is a perspective view of the assembly of invention as manufactured, mounted on a fluid handling device and sealed in a package.
Figure 6:
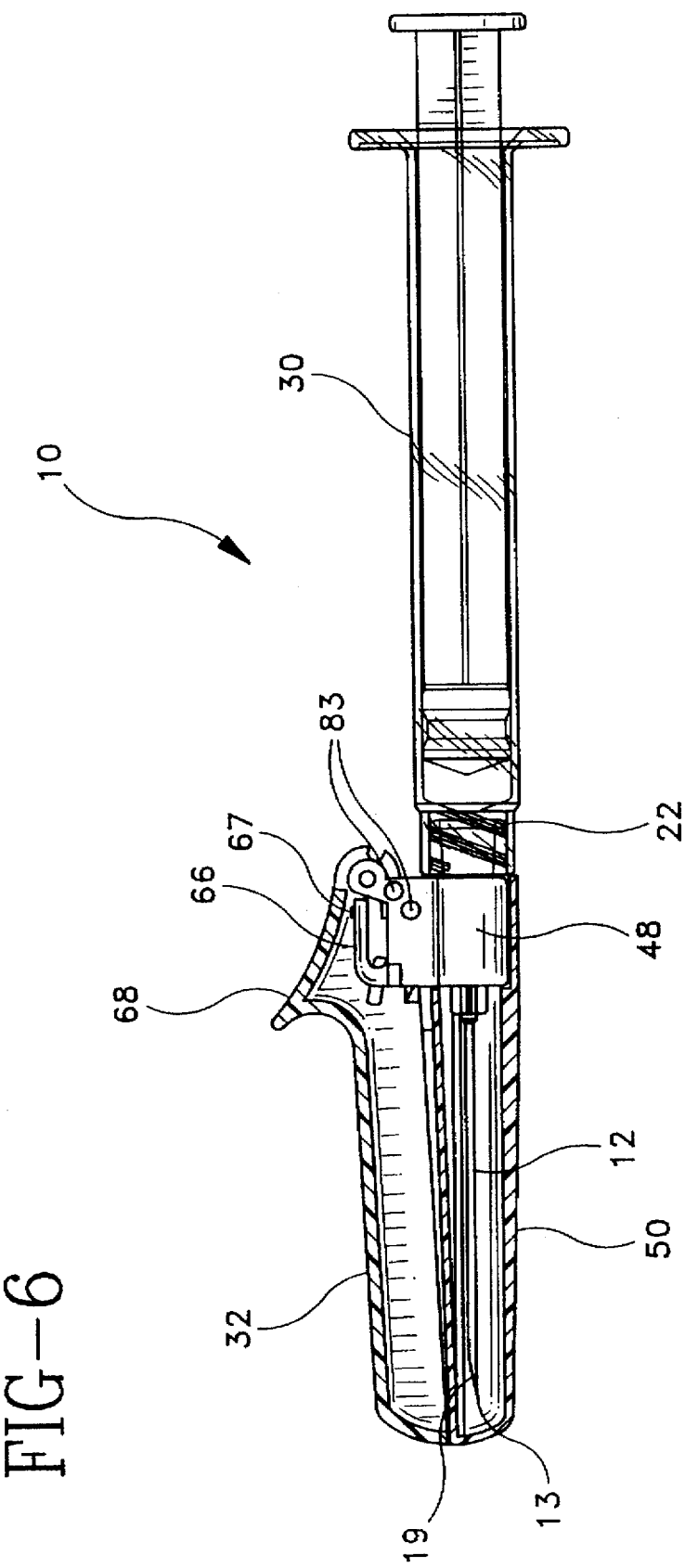
FIG. 6 is a partial longitudinal cross-sectional view of the assembly of invention mounted on a fluid handling device, taken from FIG. 2 along the line 6—6.
Figure 19:
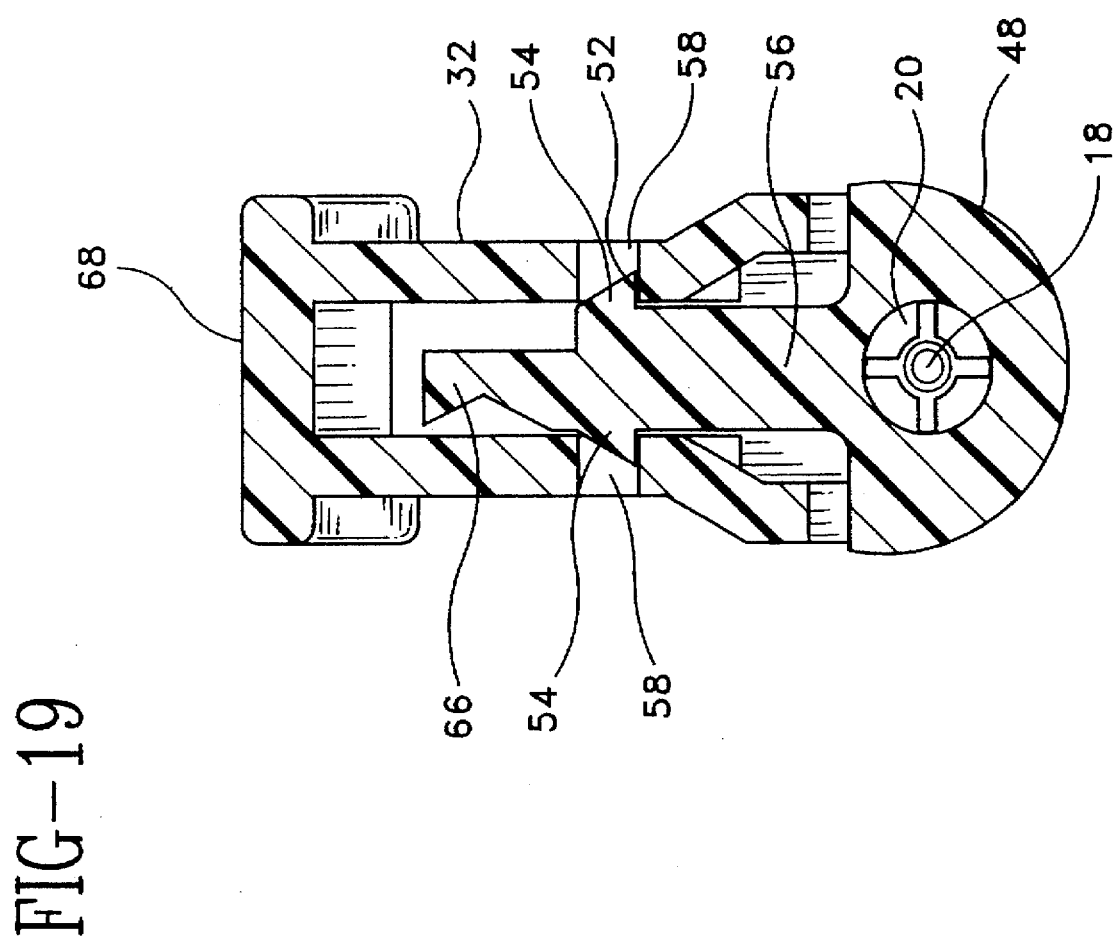
FIG. 19 is a cross-sectional view of the assembly of the invention taken from FIG. 5 along the line 19—19.

Assembly 10 has a removable cover 50 that is disposed over elongate aperture 44 in shield 32 and engages shield 32 to hold the shield in the initial closed position, best seen in FIGS. 2 and 6. Cover 50 is removable by a distal axial movement, illustrated in FIG. 3, to open shield 32, to disengage cover 50 from the shield and to expose at least sharp distal point 17 of the needle. Assembly 10 has a latch 52 for latching shield 32 to mount 48 when the practitioner is finished with needle 12. Latch 52 is formed by engaging at least one pawl 54, preferably two pawls 54, located on an outward projection 56 from mount 48 and at least one slot 58, preferably two slots 58 on shield 32. Pawls 54 and slots 58 are disposed to engage when shield 32 is pivotally moved about hinge 46 into contact with needle 12. The latched position of the shield to the mount is best seen in FIG. 16, and the engagement pawls 54 and slots 58 is shown in FIG. 19.

Hinge 46 is formed by two arms 60 projecting proximally from proximal end 34 of the shield opposite aperture 44, and each arm 60 has a hole 62. Outward projection 56 is disposed and sized to fit between arms 60 and has two outwardly extending pegs 64 that are sized and disposed to fit into holes 62 to form a pivot and to attach shield 32 to mount 48. Shield 32 is pivotally movable about hinge 46 with respect to mount 48. Projection 56 also has a cantilevered spring 66 that is disposed to engage a shoulder 67 on inside surface 40 of shield 32 and to provide a resistance to movement of shield 32 to the latched position. Preferably, cantilever spring 66 is integrally formed with mount 48 as a single unit of manufacture to simplify the assembly and increase the efficiency of the manufacturing process.

Figure 3:
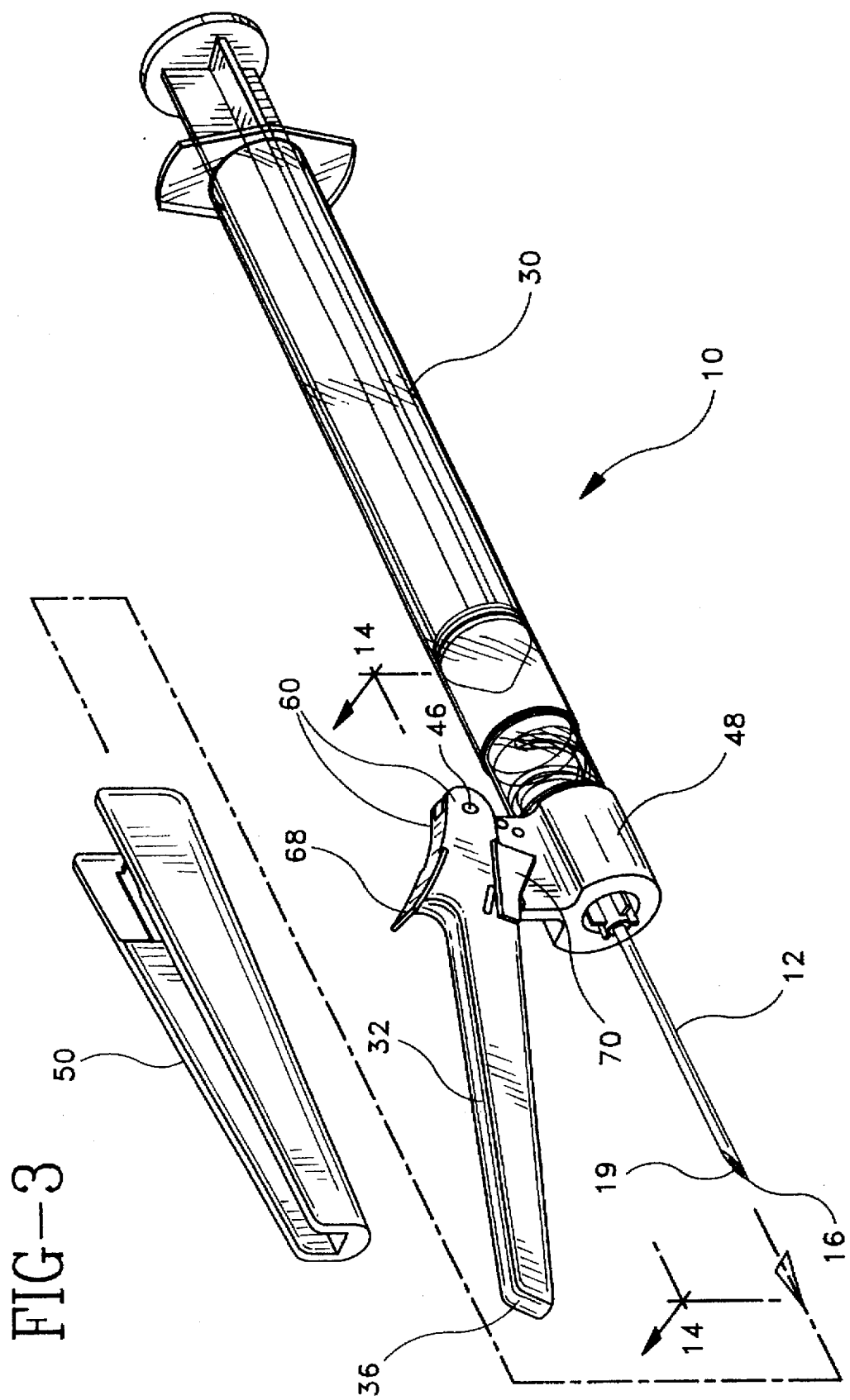
FIG. 3 is a perspective view of the assembly of the invention mounted on a fluid handling device illustrating removal of the cover and the shield in a partially open position.
Figure 4:
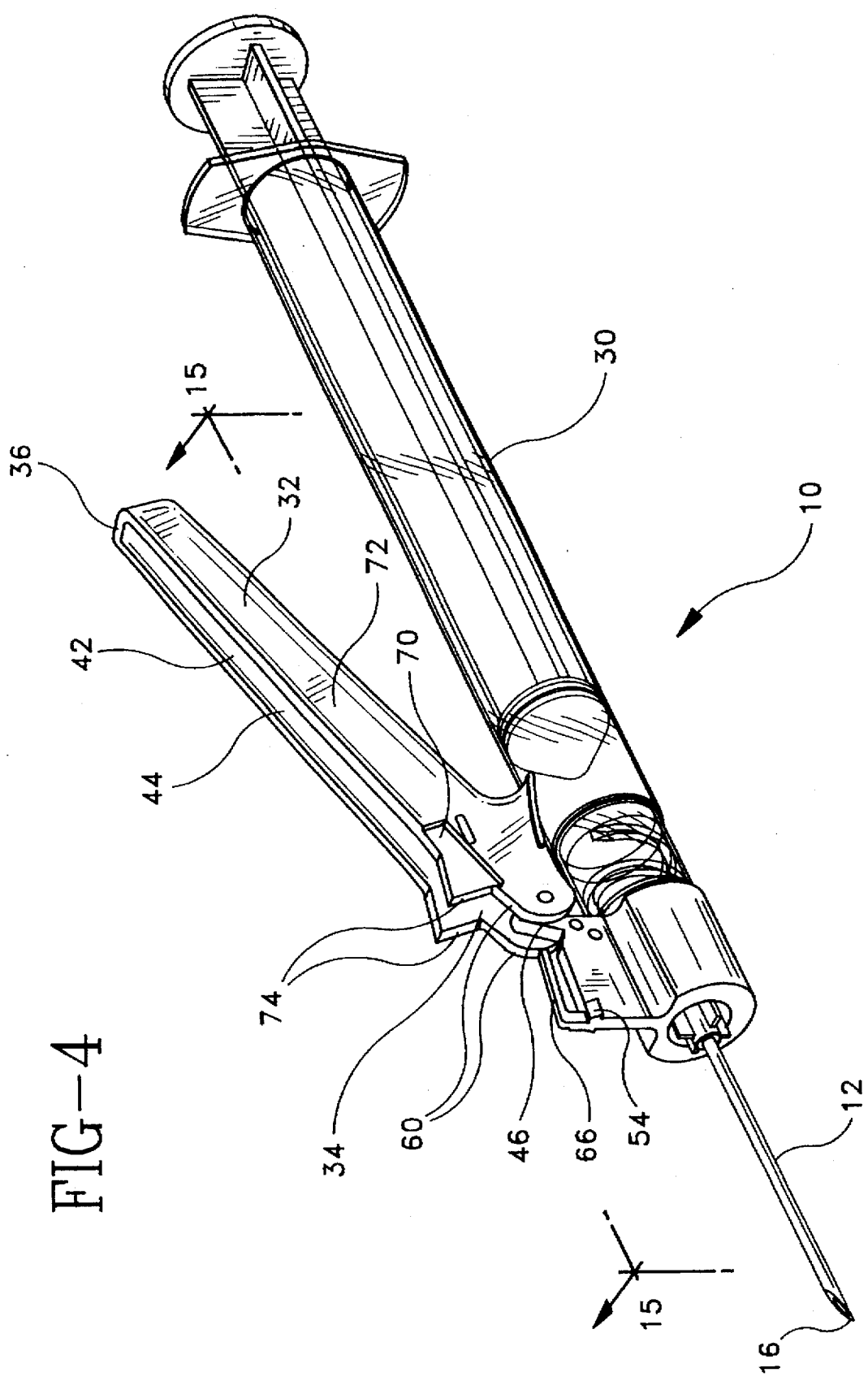
FIG. 4 is a perspective view of the assembly of the invention mounted on a fluid handling device and with the shield fully open.

Shield 32 also includes two proximal raised retention areas 70 on an exterior surface 72 of sidewall 38 adjacent to aperture 44. Raised retention areas 70 are disposed to be engaged by two rails 69 on an inside surface 51 of cover 50 to retain the cover on the shield when the assembly is in the initial closed position as seen in FIGS. 2 and 6. Cover 50 further includes at least one inward protuberance 73 that is disposed to engage a proximal edge 74 of raised retention area 70 so that when cover 50 is axially moved distally, the engagement of protuberance 73 and proximal edge 74 cause shield 32 to pivot about hinge 46 and move to the open position, as seen in FIG. 3. Once cover 50 is removed, it cannot easily be replaced with the shield in the initial closed position, because once shield 32 is moved from the initial closed position, cantilever spring 66 provides a resistance to the shield being closed unless it is sufficiently closed to engage pawls 54 with slots 58 and latch the shield onto the mount. However, cover 50 may be replaced on the mount to cover needle 12 after a syringe has been opened and filled to allow the assembly to be transported to a remote dosage location. The ability to remount cover 50 with shield 32 open is particularly useful in hospital pharmacy applications where a dosage is prepared for a patient at a location remote from the administration location. Once the dosage is administered, the practitioner then may proceed with latching the shield. The engagement of pawls 54 with slots 58 is best seen in FIG. 19.

Figure 7:
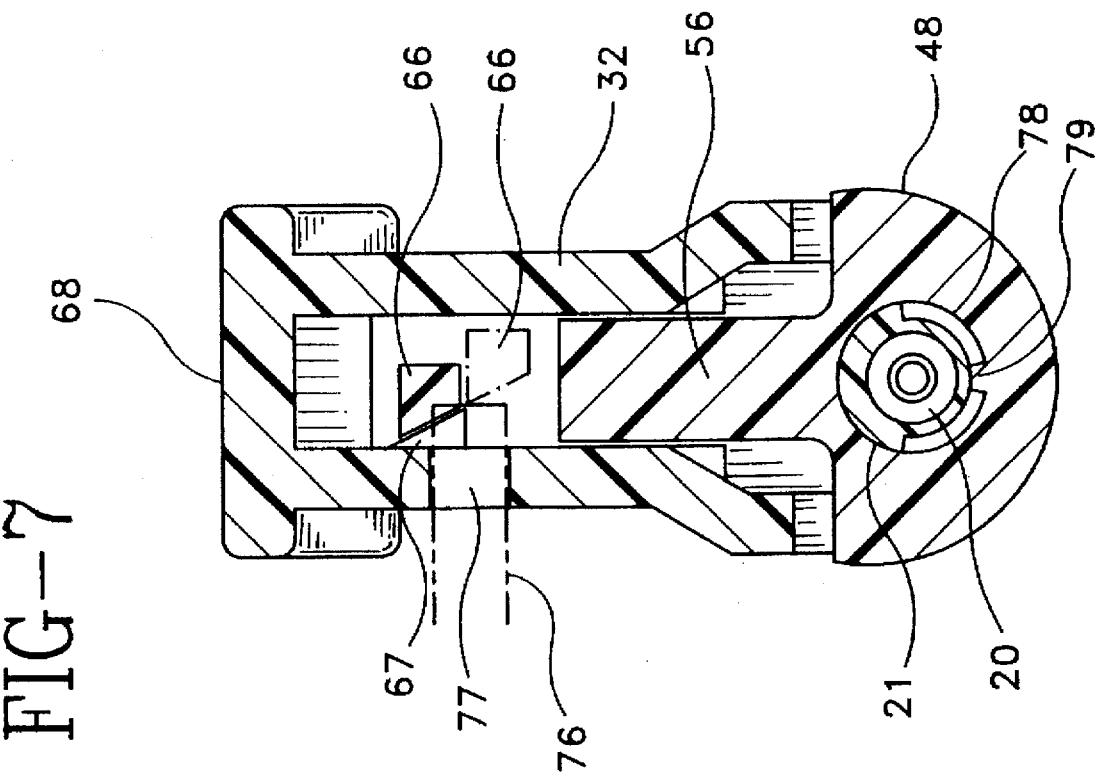
FIG. 7 is a cross-sectional view of the assembly of the invention taken from FIG. 1 along the line 7—7.
Figure 10:
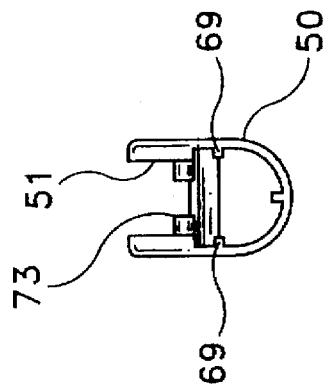
FIG. 10 is a proximal end view of the cover portion of the assembly of the invention.
Figure 8:
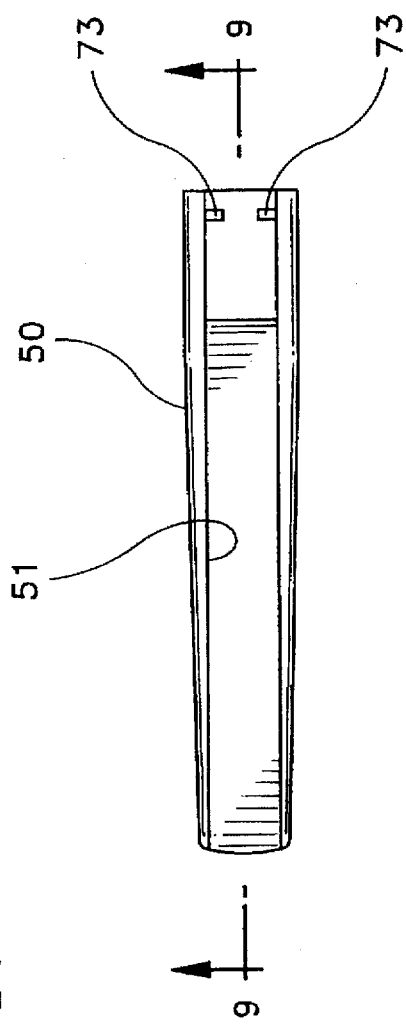
FIG. 8 is a top plan view of the cover portion of the assembly of the invention.
Figure 9:
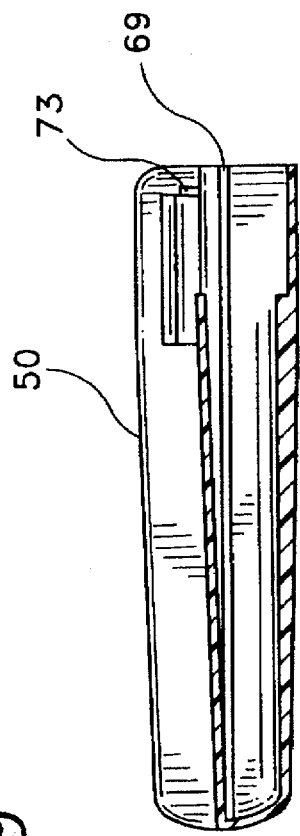
FIG. 9 is a cross-sectional view of the cover portion of the assembly of the invention taken from FIG. 8 along the line 9—9.

During the manufacturing process, since spring 66 provides resistance to shield 32 being closed, an assembly step causing deflection of spring 66 is required. The deflection of spring 66 during manufacture is illustrated in FIG. 7. Shoulder 67 extends into cavity 42 to engage spring 66. During manufacture, cover 50 is placed on shield 32 and a tool 76 (shown in phantom in FIG. 7) is positioned to enter an access port 77 in shield 32 to deflect spring 66 (schematically shown in phantom in FIG. 7). Cover 50 retains shield 32 in the initial closed position. When tool 76 is removed with shield 32 in the initial closed position, spring 66 is in its rest position (best seen in FIG. 6) where it is not under tension with shoulder 67. As cover 50 is removed and shield 32 is opened, shoulder 67 is moved past and deflects spring 66, then, when shield 32 is moved toward the closed position, spring 66 engages shoulder 67 and keeps shield 32 at least partially open until shield 32 is sufficiently closed to engage pawls 54 on slots 58 to latch the shield onto the mount. When shield 32 is latched, the closing action overcomes the resistance provided by the engagement of shoulder 67 on spring 66 and pawls 54 are engaged with slots 58 to substantially irreversibly latch shield 32 to the mount.

Shield 32 preferably includes a flange 68 that is proximally located on outside surface 41 of the shield to assist the practitioner in moving the shield from the open position to the latched position. Assembly 10 also preferably includes at least one detent in the form of at least one bump, preferably two bumps 83 to keep the shield partially open. Bumps 83 are disposed on outward projection 56 and sized to releasably interfere with at least one arm 60 to provide resistance to pivotal movement of shield 32. The resistance to the pivotal movement tends to keep the shield in position until intentionally moved by the practitioner.

Preferably, mount 48 is rotatable about needle hub 20. This rotation is best seen in FIGS. 17, 18 and 20. Opening 49 in mount 48 preferably includes an annular groove 78 on an interior surface 79 that is sized and disposed to engage a projection 21 on an exterior surface 23 of needle hub 20 when portion 53 of the needle hub is positioned in opening 49. The engagement of groove 78 and projection 21 retains the mount on the hub and allows rotation of the mount about the hub. Preferably groove 78 includes a stop 79 that is positioned to engage projection 21 and limit the rotation of mount 48 about hub 20 to less than about one rotation. The limit of the rotation of the mount about the hub facilitates a threading and unthreading for mounting and dismounting the needle hub onto a fluid handling device. The preferred rotatability of the mount about the needle hub allows the practitioner to position shield 32 with respect to a bevel 19 of sharp distal point 17 of the needle. The ability to position shield 32 with respect to needle bevel 19 is particularly important for procedures such as blood drawing and the like where needle bevel position is important to the success of the procedure. Since, preferably, shield 32 may be rotatably positioned about the hub as well as pivotally opened and closed, shield 32 may be moved to allow practitioners to position the shield according to their needs. If mount 48 was not rotatable about the hub and needle bevel 19 placement is critical, an additional constraint of needle bevel orientation is imposed on the manufacturing process.

Alternatively, for applications where needle bevel placement is not critical to the procedure, mount 48 may be fixedly attached to hub 20. Referring to FIG. 21, hub 20 may be fixedly attached into opening 49 in mount 48 by techniques including, but not limited to, an adhesive bond; a mechanical interference fit between the needle hub and the opening; a solvent bond between the needle hub and the opening; a thermal weld between the needle hub and the opening; an ultra-sonic weld between the needle hub and the opening; and a mechanical snap-fit between the needle hub and the opening.

Figure 22:
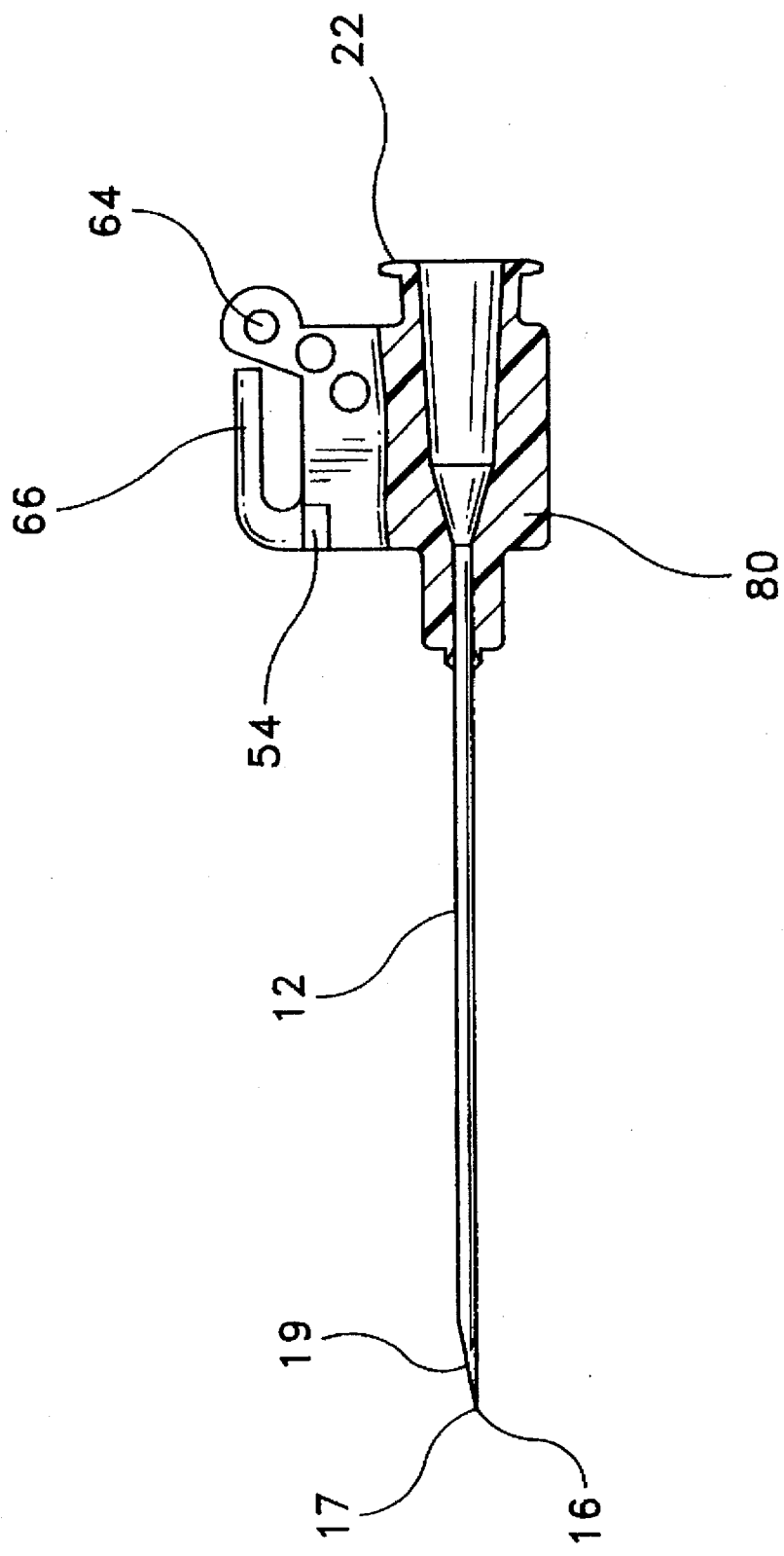
FIG. 22 is a partial cross-sectional view of the mount and hub portion of another embodiment of the invention analogous to the views of FIGS. 20 and 21.

A further alternative is illustrated in FIG. 22, where all the elements of hub 48 and needle hub 20 are integrally formed in a unitary structure 80.

Figure 23:
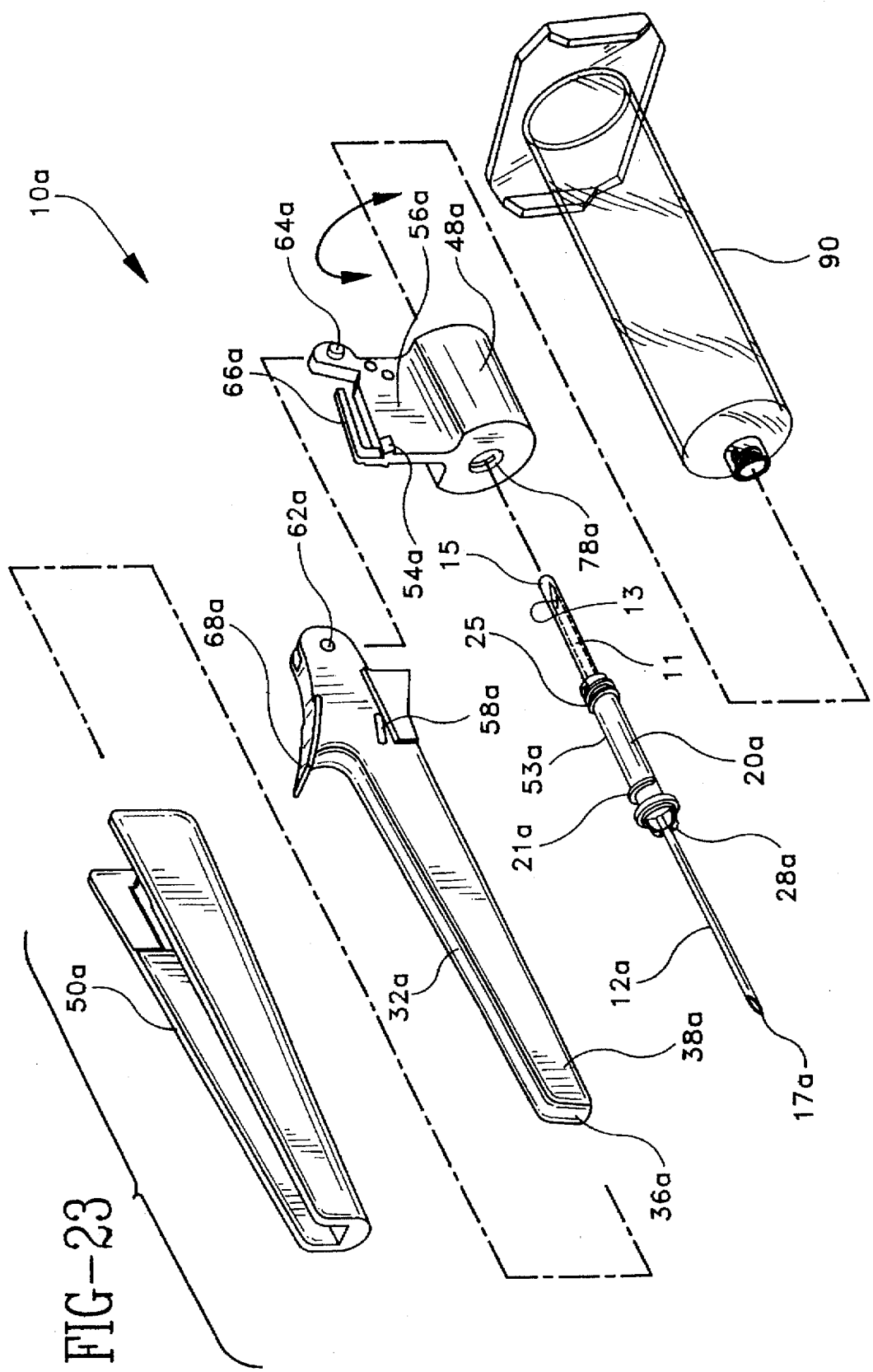
FIG. 23 is an exploded perspective view of an embodiment of the invention suitable for mounting on a needle holder.

Another alternate embodiment that is particularly directed toward phlebotomy is shown in FIG. 23. In this embodiment, there are elements similar in structure and function to the embodiment of the present invention shown in FIGS. 1–20. Accordingly, substantially similar components that perform substantially similar functions are numbered identically to those components of the embodiment of FIGS. 1–20 except that a suffix "a" is added to identify those components in FIG. 23. Assembly 10a includes shield 32a and mount 48a. In this embodiment, needle 12a has a proximal portion 11 with a sharp distal point 17a and a flow control valve 15 to occlude flow through the needle. Assembly 10a also has needle 12a disposed in axial bore 28a in hub 20a so both that the sharp proximal point 13 and the distal sharp point 17a project from the hub. Needle hub 20a includes external distal threads 25 for mounting hub 20a into a needle holder 90. Needle holder 90 is useful for filling evacuated blood collection tubes that are mounted in needle holder 90 and onto the distal portion 11 of the needle displacing flow control valve 15.

The shield, mount, and needle hub of the invention may be formed from polymeric materials such as thermoplastic resins, cast resins and the like. Suitable thermoplastic resins include, but are not limited to, polypropylene, polyethylene, acrylonitrile-butadiene-styrene, polycarbonate, polystyrene and the like. Polypropylene and polyethylene are preferred thermoplastic resins when injection molding is selected as the forming technique. For some applications, polycarbonate resin may be preferred for applications where transparency and rigidity are required. Needles suitable for use in the assembly may be formed from stainless steel. In assembly 10, needle 12 is fixedly attached to hub 20. Suitable methods for fixedly attaching the needle to the hub include, but are not limited to, adhesive bonding and insert molding the needle into the hub. Preferably, needle 12 is adhesively bonded into hub 20.

Referring again to FIG. 2, assembly 10 may be placed on a fluid handling device such as syringe 30 and sealed in a package 92 formed from materials substantially resistant to the passage of microorganisms. The packaged assembly may then be exposed to conditions that render any microorganisms in the package non-viable. Assembly 10 is then considered sterile until package 92 is opened. Suitable materials for forming package 92 include, but are not limited to, paper, thermoplastic film, spun-bonded polyolefin non-woven and the like. Suitable conditions for rendering microorganisms non-viable include, but are not limited to, exposure to chemical sterilants such as ethylene oxide, gaseous hydrogen peroxide and the like and exposure to ionizing radiation such as gamma radiation and beta radiation. Selection of packaging materials and the materials for formation of the assembly should take prospective sterilization The shielded needle assembly of the invention is simple to manufacture and easy to use. The assembly allows practitioners to intuitively uncover the needle for use by removing the cover then to reshield needles and latch the shield to the mount substantially without placing their hands in close proximity to, or beyond, the distal point of the needle, thus encouraging the practitioners to shield the needle after use. In clinical settings where pointed needles are routinely used, use of shielded assemblies of the invention may provide reductions of exposures to unshielded needles to both practitioners using needles and to support personnel who may unexpectedly encounter used needles.

What is claimed is:

1. A needle assembly comprising:

an elongate needle having a proximal end, a distal end and a passageway therethrough defining an axis:

a needle hub having a proximal end, a distal end and an exterior surface, said needle hub having an axial bore therethrough to receive and hold said needle with said distal end of said needle projecting axially therefrom, said proximal end of said needle hub further including means for releasably mounting said needle hub on a fluid handling device;

an elongate shield having an open proximal end, a distal end and a sidewall with an inside surface defining a cavity, said sidewall having an elongate aperture into said cavity from about said distal end to said proximal end;

hinge means including a mount for retaining said shield onto said hub, said mount including an opening therein sized and shaped to receive at least a portion of said needle hub, said shield being movable about said hinge means by an off-axis pivotal movement between an initial closed position wherein inadvertent access to said needle is substantially prevented, an open position wherein at least said distal point of said needle is exposed and a latched position wherein said shield is in contact with said needle, is latched to said mount and substantially prevents access to said distal point of said needle;

a removable cover, said cover disposed over said elongate aperture in said shield and engaging said shield to hold said shield in said initial closed position, said cover being removable by a distal axial movement to open said shield, to disengage said cover from said shield and to expose at least said distal point of said needle; and latch means for latching said shield to said mount when said shield is in said latched position.

2. The needle assembly of claim 1 wherein said hinge means comprises two arms projecting proximally from said proximal end of said shield opposite said aperture, said each arm having a hole therethrough and wherein said mount comprises an outward projection disposed to fit between said arms, said projection having two outwardly extending pegs, said pegs being sized and disposed to fit into said holes to form a pivot and to attach said shield to said mount said shield being movable with respect to said mount about said pivot.

3. The needle assembly of claim 2 wherein said outward projection on said mount further comprises a cantilevered spring disposed to engage said inside surface of said shield and to provide a resistance to movement of said shield to said latched position.

4. The needle assembly of claim 3 wherein said cantilevered spring is integrally formed as a single unit of manufacture with said mount.

5. The needle assembly of claim 3 wherein said latch means comprises at least one pawl on said outward projection on said mount and at least one slot located on said arm on said shield, said pawl and said slot being disposed to engage when said shield is moved to contact said needle.

6. The needle assembly of claim 5 wherein said latch means comprises two pawls on said outward projection on said mount and said two arms each having a slot disposed to engage one of said pawls on said outward projection.

7. The needle assembly of claim 1 wherein said shield includes an exterior flange on said sidewall opposite said aperture, said flange to facilitate an operator's movement of said shield from said open position to said latched position.

8. The needle assembly of claim 1 wherein said shield further comprises proximal raised retention areas on an exterior surface of said sidewall adjacent said aperture and an interior surface of said cover includes rails disposed to engage said retention areas on said shield when said cover is positioned on said shield in said initial closed position.

9. The needle assembly of claim 8 wherein said cover further comprises at least one inward protuberance on said interior surface of said cover disposed to engage a proximal edge of said raised retention area when said cover is moved distally thereby to pivot said shield to said open position.

10. The needle assembly of claim 1 wherein said needle hub is integrally formed with said mount.

11. The needle assembly of claim 1 wherein said means for releasably mounting said needle hub on the fluid handling device comprises a female luer fitting.

12. The needle assembly of claim 1 wherein said distal end of said shield is closed.

13. The needle assembly of claim 1 further including means for fixedly attaching said mount on said needle hub, said means for fixedly attaching being selected from the group consisting of an adhesive bond between said needle hub and said opening; a mechanical interference fit between said needle hub and said opening; a solvent bond between said needle hub and said opening; a thermal weld between said needle hub and said opening; an ultra-sonic weld between said needle hub and said opening; and a mechanical snap-fit between said needle hub and said opening.

14. The needle assembly of claim 1 further including means for retaining said mount on said needle hub comprising an annular groove on an interior surface of said axial opening in said mount and a projection on said exterior surface of said needle hub disposed and sized to engage said groove when said portion of said needle hub is positioned in said opening, said engagement of said projection in said groove thereby retaining said mount on said hub and allow rotation of said mount about said hub.

15. The needle assembly of claim 14 wherein said groove and said projection further include means to limit annular rotation of said mount about said hub to less than about one rotation.

16. The needle assembly of claim 15 wherein said limit means comprises a stop in said groove positioned to engage said projection on said hub.

17. The needle assembly of claim 16 wherein said elongate needle comprises a sharp distal end and a sharp proximal end, with said needle disposed in said axial opening in said hub so that said sharp distal end projects distally from said hub and said sharp proximal end projects proximally from said hub.

18. The needle assembly of claim 17 wherein said means for releasably attaching said needle hub to the fluid handling device includes male threads on said exterior surface of said hub.

19. A needle assembly comprising:

an elongate needle having a proximal end, a distal end and a passageway therethrough defining an axis;

a needle hub having a proximal end, a distal end and an exterior surface, said needle hub having an axial bore therethrough to receive and hold said needle with said distal end of said needle projecting axially therefrom, said proximal end of said needle hub further including means for releasably mounting said needle hub on a fluid handling device;

an elongate shield having an open proximal end, a distal end and a sidewall with an inside surface defining a cavity, said sidewall having an elongate aperture into said cavity from about said distal end to said proximal end said shield further comprising two arms projecting proximally from said proximal end of said shield opposite said aperture, said each arm having a hole therethrough;

hinge means including a mount for retaining said shield onto said hub, said mount including an opening therein sized and shaped to receive at least a portion of said needle hub, said shield being movable about said hinge means by an off-axis pivotal movement between an initial closed position wherein inadvertent access to said needle is substantially prevented, an open position wherein at least said distal point of said needle is exposed and a latched position wherein said shield is in contact with said needle, is latched to said mount and substantially prevents access to said distal point of said needle, said mount further comprising an outward projection disposed to fit between said arms on said shield, said projection having two outwardly extending pegs, said pegs being sized and disposed to fit into said holes in said arms to form a pivot and to attach said shield to said mount, said shield being movable with respect to said mount about said pivot;

a removable cover, said cover disposed over said elongate aperture in said shield and engaging said shield to hold said shield in said initial closed position, said cover being removable by a distal axial movement to open said shield, to disengage said cover from said shield and to expose at least said distal point of said needle; and latch means for latching said shield to said mount when said shield is in said latched position, said latch means comprising two pawls on said outward projection and one slot located on said each arm of said shield, said pawls and said slots being disposed to engage when said shield is moved to contact said needle.

20. The needle assembly of claim 19 wherein said outward projection on said mount further comprises an integrally formed cantilevered spring disposed to engage said inside surface of said shield and to provide a resistance to movement of said shield to said latched position.

* * * * *